United States Patent [19]

Waeber et al.

[11] Patent Number: 4,839,343
[45] Date of Patent: Jun. 13, 1989

[54] PREPARATION CONTAINING HEXATRIACONTAPEPTIDES AND METHODS OF USE

[75] Inventors: Bernard Waeber, Marly; Hans R. Brunner, Pully, both of Switzerland

[73] Assignee: Debiopharm, S.A., Lausanne, Switzerland

[21] Appl. No.: 25,305

[22] Filed: Mar. 13, 1987

[51] Int. Cl.$^4$ .................. A61K 37/02; C07K 7/10
[52] U.S. Cl. ........................... 514/12; 530/324
[58] Field of Search ................... 514/12; 530/324

[56] References Cited

U.S. PATENT DOCUMENTS 4,701,441  10/1987  Kalra ........................ 514/12

OTHER PUBLICATIONS

Tatemoto, Proc. Natl. Acad. Sci. U.S.A., vol. 79, pp. 5485–5489, (9/1982).
Gray et al., Life Sciences, vol. 38, pp. 389–401, (1986).
D. Evequoz, et al., "Neuropeptide y Prevents Blood Pressure Fall Induced by Endotoxin in Conscious Rats with Adrenal Medullectomy," *Clinical Research*, vol. 34, No. 2, Apr., 1986, p. 628A.

*Primary Examiner*—Delbert R. Phillips
*Assistant Examiner*—Christina Chan
*Attorney, Agent, or Firm*—Pennie & Edmonds

[57] ABSTRACT

Preparation containing hexatriacontapeptides suitable for intravenous administration to human or other animal subjects are disclosed. such compositions are effective in treating life-threatening hypotension as encountered in bacteremic, anaphylactic or cardiogenic shock.

14 Claims, No Drawings

PREPARATION CONTAINING HEXATRIACONTAPEPTIDES AND METHODS OF USE

TECHNICAL FIELD

The invention relates to pharmaceutical compositions and more particularly, to hextricontapeptides in solution for intravenous administration to a subject for the treatment of hypotension.

BACKGROUND OF THE INVENTION

The present invention relates to compositions containing certain hexatriacontapeptides (linear peptides each composed of thirty-six amino acids) which have been recently described as neuropeptides, and more specifically neuropeptide Y (NPY) of porcine or human origin and peptide YY (PYY).

The structure of NPY (porcine), has been established as being:

Tyr—Pro—Ser—Lys—Pro—Asp—Asn—Pro—Gly—Glu—
 1    2    3    4    5    6    7    8    9   10

—Asp—Ala—Pro—Ala—Glu—Asp—Leu—Ala—Arg—Tyr—
  11   12   13   14   15   16   17   18   19   20

—Tyr—Ser—Ala—Leu—Arg—His—Tyr—Ile—Asn—Leu—
  21   22   23   24   25   26   27   28   29   30

—Ile—Thr—Arg—Gln—Arg—Tyr—$NH_2$
  31   32   33   34   35   36 or alternatively, according to the recommendations of the IUPAC-IUB Joint Commission on Nomenclature of amino acids and peptides (Eur. J. Biochem. 1984, 138, 9), with one-letter symbols:

```
Y P S K P D N P G E—
—D A P A E D L A R Y—
—Y S A L R H Y I N L—
—I T R Q R Y  (amide).
```

The structure of NPY (human) differs from the above in having Met(M) instead of Leu(L) in position 17.

The structure of PYY is known to be:

Tyr—Pro—Ala—Lys—Pro—Glu—Ala—Pro—Gly—Glu—

—Asp—Ala—Ser—Pro—Glu—Glu—Leu—Ser—Arg—Tyr—

—Tyr—Ala—Ser—Leu—Arg—His—Tyr—Leu—Asn—Leu—

—Val—Thr—Arg—Gln—Arg—Tyr—$NH_2$ or, in one-letter symbols:

```
Y P A K P E A P G E—
—D A S P E E L S R Y—
—Y A S L R H Y L N L—
—V T R Q R Y  (amide).
```

A variety of pharmacologic activities have been described for NPY and PYY, notably vasoconstrictor effects, natriuretic properties, stimulation of feeding and drinking behaviour, hypertensive effects at high doses and neutrotransmitter or neuromodulator properties.

We have surprisingly found that these peptides, and in particular NPY, when injected into animals at non-pressor doses, almost completely prevent the blood pressure fall induced by endotoxin, such blood pressure fall being frequently lethal to non-treated subjects.

It is a well-known fact, both in animals and in humans, that non-treated hypotension resulting from bacteremic and septic shock, or from anaphylactic, hypovolemic or cardiogenic shock, is frequently fatal.

A common treatment in such cases is the injection or infusion of vasoactive drugs, such as alpha-receptor agonists or antagonists and dopaminergic or beta-receptor stimulants, generally known as inotropic and vasoactive amines.

Such agents however, while counteracting to some extent the hypotensive shock, suffer from the limitation that they affect heart rate which rises frequently to unacceptable levels, requiring th discontinuation of their adminstration. This, in part, explains why presently available therapies have limited efficacy, resulting in a disturbingly high proportion of fatalities. In addition the effect of vasoactive amines is known to wear off with time, thus necessitating repeated administration to obtain the desired results.

The methods of treatment of the present invention improve the therapeutic outcome of such life-threatening conditions, not only because they prevent the severe hypotension which may be fatal, but also because they allow the reduction of doses of vasoactive amines to levels which do not significantly increase the heart rate of the subject.

SUMMARY OF THE INVENTION

It has now been discovered that compositions containing hexatriacontapeptides selected from the group of neuropeptide Y (porcine or human) and peptide YY, suitably adapted for parenteral, and in particular intraveous administration, are beneficial for the treatment of life-threatening hypotension frequently seen in bacteremic, anaphylactic an aphylactoid or cardiogenic shock. A surprising feature of this invention is the prevention, in certain cases, of such fatal hypotension at doses which, per se, are non-pressor doses.

Another surprising feature of the present invention is the possibility of reducing the effective doses of concomittantly administered vasoactive amines to levels not appreciably affecting the heart rate of the patient.

These peptide compositions are adapted for parenteral or intravenous administration and are formulated with physiologically acceptable, non-alkaline diluents which are at the same time solvents for said peptides and compatible with inotropic catecholamines, such as norepinephrine, epinephrine, dopamine, dobutamine hydrochloride or derivatives thereof, as well as with other vasoactive amines, which may be co-administered with said peptides. Preferably, these solutions possess a pH between about 2.5 and 5.5.

DESCRIPTION OF PREFERRED EMBODIMENTS

The hexatriacontapeptides of the present invention are selected from the group of NPY (porcine, human) and PYY.

Their structure has been described in the literature (see for intstance T. S. Gray and J. E. Morley, Life Sciences 38, 389–401, 1986; I. D. Glover et al., J. Biochem. 142, 379–385, 1985) and are herein given with the three-letter or one-letter symbols according to the IUPAC-IUB recommended nomenclature (Eur. J. Biochem. 138, 9, 1984).

The putative role of NPY (and PYY) in regulating autonomic function has been reviewed by T. L. O'-Donohue et al. (Peptides, 6, 755–768, 1985).

The compositions of the present invention are characterized by the fact that they contain the hexatriacontapeptides in a solution suitable for parenteral or intravenous administration and such that the solvent is not only physiologically acceptable and non-toxic but that it is non-alkaline and compatible with an inotropic catecholamine, such as epinephrine, dopamine or other vasoactive amines which may be therefore co-administered with said hexatriacontapeptides. Such non-alkaline diluent may conveniently be an antioxidant such as 1% sodium bisulfite an ascorbic acid in sterile water, saline, or 5% dextrose solution.

Particularly in the treatment of bacteremic septic shock, it is also important that such non-alkaline diluent be compatible with an antibiotic, for example, an aminoglycoside such as Gentamicin, a cephalosporin such as Cefazolin, or a broad spectrum penicillin such as Carbenicillin, which may then be co-administered.

The concentration of peptide in the solution preferably ranges from between about 0.01 and 1 percent by weight, so that it is present in sufficient quantities to administer to the subject an amount in the range of between 0.01 and 50 pmol/kg/min. As one skilled in the art would realize, these levels are substantially lower than the normal amounts of the peptide which would be administered for its usual effects, i.e. vasoconstriction, natriuretics, etc.

Similarly, the amount of vasoactive amine in the solution can also used at the same weight percent levels so that the subject receives between about 0.001 and 1 mg/min during administration of the peptide solution.

In actual use, these solutions would be prepared with the correct amount of diluent according to the weight of the patient in order to achieve the desired rate of administration of the peptide and vasoactive amine.

In addition, known amounts of antioxidants and/or antibiotic agents can be included in these solutions.

The following examples are provided to illustrate the present invention but are not limitative, as it will be apparent to those skilled in the art.

EXAMPLE 1

Normotensive male Wistar rats were subjected to adrenal demedullation on the right side and either adrenolectomized or sham-operated on the left side. Ten days later a solution of NPY in non-alkaline saline was given as an intravenous infusion (70 ng/min) to these conscious semi-restrained animals. A group of control animals received only the saline diluent. During the last 75 minutes of the experiment, endotoxin (LPs $E.$ $Coli$ 0111: B4, 10 mcg/min i.v.) was administered both in NPY-treated and control animals. Intraarterial mean blood pressure before endotoxin infusion was 116±1.6 mm Hg. In the 12 NPY treated rats the blood pressure was reduced by only 8±2.1 mm Hg whereas the drop in the nine control animals was impressive, causing the death of two animals and being 40±6.4 mm Hg lower in the remaining seven. In another group of rats a similar infusion of NPY solution (70 ng/min) had no significant effect on blood pressure.

These results indicate a preventive effect of NPY, given at non-pressor doses, against the hypotensive effect caused by endotoxin.

EXAMPLE 2

Conscious normotensive rats were divided into six groups. Rats of Group II and IV were infused intravenously with NPY (0.1 mcg/min for 75 min). A further two groups of rats (I and III) received the vehicle of the peptide (10 mcg/min) for the same period. *Escherichia Coli* endotoxin (lipopolysaccharide *E. Coli* 0.111: B4, Difco Laboratories, Detroit, MI), 10 mcg/10 mcl/min was infused starting 15 min after the beginning of the NPY-infusion (Group IV) or its vehicle (Group III). The remaining rats (Groups I and III) were given the vehicle of endotoxin, 10 mcl/min i.v. In all these rats, a dose-response curve to intravenous injections of norepinephrine was obtained 5 min after ending the administration of NPY. The infusion of endotoxin or its vehicle was continued throughout this period. In two additional groups rats infused for 45 min with endotoxin or its vehicle, a 2 ml blood sample was obtained via the arterial catheter for determination of plasma NPY levels.

The endotoxin was dissolved in 0.9% NaCl to achieve a concentration of 10 mg/l. NPY was diluted with 0.1M HCl to a concentration of 10 mg/l. Aliquots containing 15 mcg were stored frozen at −70° C. and thawed immediately before use. The different solutions were infused using a syringe pump (Model 455, Sage Instrument, White Plains, NY). Norepinephrine (Arterenol, Hoechst, Frankfurt-am-Main, FRG) was diluted in 0.9% NaCl to attain a concentration of 20 ng/20 mcl. Using a 250 mcl glass syringe (Hamilton), the dose of norepinephrine was increased by altering the volume injected.

The infusions of endotoxin and NPY whether given alone or in combination had no significant effect on blood pressure or heart rate. Blood pressures measured immediately before the bolus injections of norepinephrine were similar in all groups of rats.

As expected, rats receiving no active substance (Group I) showed a dose-related rise in blood pressure following injections of norepinephrine. In contrast, the rats administered endotoxin alone (Group III) exhibited a remarkable attenuation of the pressor response to all doses of norepinephrine ($p<0.001$). However, when endotoxin-treated rats received a simultaneous NPY infusion (Group IV), the blood pressure response to norepinephrine was significantly greater than in those animals receiving endotoxin alone ($p<0.05$, $<0.01$, $<0.01$ and $<0.05$ for the doses of 20, 40, 80 and 160 ng respectively). The shift in the dose-response curve produced by infusing NPY in these endotoxin-treated rats was such that there was no longer any significant difference in the blood pressure response to norepinephrine between these animals (Group IV) and the control rats (Group I) who received no active substance. This was true for all doses tested.

Compared with the control responses (Group I), NPY infused alone (Group II) significantly enhanced the subsequent pressor effects of all doses or norepinephrine ($p<0.001$, $<0.01$, $<0.001$ and $<0.05$ for the doses of 20, 40, 80 and 160 ng respectively). This NPY-induced facilitation of norepinephrine evoked changes in blood pressure is long-lasting since the last dose of norepinephrine was administered 50 min after stopping the NPY infusion.

EXAMPLE 3

A patient seriously affected by bacteremic (endotoxic) shock was admitted in an intensive care unit and treated with dopamine given intravenously at doses of 10 and 20 mcg/kg/min. In spite of such treatment the arterial pressure of the patient continued to fall.

A solution of NPY was then given by intravenous infusion at increasing doses of 0.01 to 50 pmol/kg/min over a period of 10 hours. The treatment resulted in a normalization of arterial pressure and allowed a decrease in the dose of dopamine each time that tachycardia was observed.

In another patient a similar treatment with PYY was also found to be beneficial.

While it is apparent that the invention here disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A method for increasing the blood pressure of a subject experiencing hypotension which comprises administering to said subject a therapeutically effective amount of a composition comprising:

a peptide of the formula

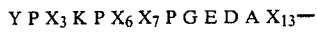

Y P $X_3$ K P $X_6$ $X_7$ P G E D A $X_{13}$—

—$X_{14}$ E $X_{16}$ $X_{17}$ $X_{18}$ R Y Y $X_{22}$ $X_{23}$ L R H—

—Y $X_{28}$ N L $X_{31}$ T R Q R Y (amide)

wherein $X_3$ is A or S; $X_6$ is E or D; $X_7$ is A or N; $X_{13}$ is S or P; $X_{14}$ is P or A; $X_{16}$ is E or D; $X_{17}$ is L or M; $X_{18}$ is S or A; $X_{22}$ is A or S; $X_{23}$ is S or A; $X_{28}$ is L or I; and $X_{31}$ is V or I; said peptide present in a therapeutically effective amount for treatment of hypotension but below that which would induce vasoconstrictor effects or natriuretic, neurotransmitter or neuromodulator properties in said subject; and a physiologically acceptable diluent as a solvent for said peptide; said diluent also being compatible with vasoactive amines; said composition administered for a time sufficient to increase the blood pressure of the subject to a predetermined satisfactory level.

2. The method of claim 1 wherein said composition is administered parenterally, and wherein the amount of the peptide to be administered ranges from about 0.01 to 50 pmol/kg/min.

3. The method of claim 1 wherein the hypotension is caused by bacteremia, cardiovascular disease, or a reaction to anaphylaxis or anaphylactoid shock.

4. The method of claim 1 wherein said solution has a pH of between about 2.5 and 5.5.

5. The method of claim 1 wherein the composition further comprises a vasoactive amine which is administered to the subject in an amount of between about 0.001 and 1 mg/min.

6. The method of claim 1 wherein the composition further comprises an antioxidant of sodium bisulfate or ascorbic acid, and an antibiotic agent of an amino glycoside, a cephalosporin or a broad spectrum penicillin.

7. A method for increasing the blood pressure of a subject experiencing hypotension which comprises administering parenterally to said subject a pharmaceutical composition in the form of a solution which comprises:

a peptide of the formula

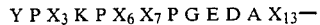
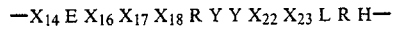

Y P $X_3$ K P $X_6$ $X_7$ P G E D A $X_{13}$—

—$X_{14}$ E $X_{16}$ $X_{17}$ $X_{18}$ R Y Y $X_{22}$ $X_{23}$ L R H—

—Y $X_{28}$ N L $X_{31}$ T R Q R Y (amide)

wherein $X_3$ is A or S; $X_6$ is E or D; $X_7$ is A or N; $X_{13}$ is S or P; $X_{14}$ is P or A; $X_{16}$ is E or D; $X_{17}$ is L or M; $X_{18}$ is S or A; $X_{22}$ is A or S; $X_{23}$ is S or A; $X_{28}$ is L or I; and $X_{31}$ is V or I; said peptide present in a therapeutically effective amount of between about 0.01 and 1 weight percent for treatment of hypotension but below that which would induce undesirable vasocontrictor effects in said subject; and a physiologically acceptable diluent as a solvent for said peptide; said diluent also being compatible with vasoactive amines and including an antioxidant or antibiotic agent therein; said composition administered for a sufficient time to increase the blood pressure of the subject to a predetermined satisfactory level, without causing an unacceptable, life threatening rise in the heart rate of the subject.

8. A method for increasing the blood pressure of a subject experiencing hypotension which comprises administering parenterally to said subject a pharmaceutical composition in the form of a solution which comprises:

a peptide of the formula

Y P $X_3$ K P $X_6$ $X_7$ P G E D A $X_{13}$—

—$X_{14}$ E $X_{16}$ $X_{17}$ $X_{18}$ R Y Y $X_{22}$ $X_{23}$ L R H—

—Y $X_{28}$ N L $X_{31}$ T R Q R Y (amide)

wherein $X_3$ is A or S; $X_6$ is E or D; $X_7$ is A or N; $X_{13}$ is S or P; $X_{14}$ is P or A; $X_{16}$ is E or D; $X_{17}$ is L or M; $X_{18}$ is S or A; $X_{22}$ is A or S; $X_{23}$ is S or A; $X_{28}$ is L or I; and $X_{31}$ is V or I; said peptide present in a therapeutically effective amount of between about 0.01 and 1 weight percent for treatment of hypotension but below that which would induce undesirable vasoconstrictor effects in said subject; a vasoactive amine in a therapeutically effective amount to counteract hypotensive shock in said subject but less than that which would cause an unacceptable, life threatening rise in the heart rate of said subject; and a physiologically acceptable diluent as a solvent for said peptide; said diluent also being compatible with said vasoactive amine and including an antioxidant or antibiotic agent therein; said composition administered for a sufficient time to increase the blood pressure of the subject to a predetermined satisfactory level, without causing an unacceptable, life threatening rise in the heart rate of the subject.

9. A method for increasing the blood pressure of a subject experiencing hypotension which comprises administering parenterally to said subject a pharmaceutical composition in the form of a solution which comprises:

a peptide of the formula

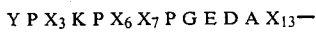
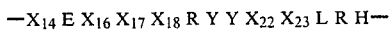
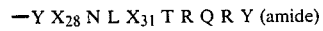

Y P $X_3$ K P $X_6$ $X_7$ P G E D A $X_{13}$—

—$X_{14}$ E $X_{16}$ $X_{17}$ $X_{18}$ R Y Y $X_{22}$ $X_{23}$ L R H—

—Y $X_{28}$ N L $X_{31}$ T R Q R Y (amide)

wherein $X_3$ is A or S; $X_6$ is E or D; $X_7$ is A or N; $X_{13}$ is S or P; $X_{14}$ is P or A; $X_{16}$ is E or D; $X_{17}$ is L or M; $X_{18}$ is S or A; $X_{22}$ is A or S; $X_{23}$ is S or A; $X_{28}$ is L or I; and $X_{31}$ is V or I; said peptide present in a therapeutically effective amount of between about 0.01 and 1 weight percent for treatment of hypotension but below that which would induce undesirable vasoconstrictor effects in said subject; a vasoactive amine in a therapeutically effective amount to counteract hypotensive shock in said subject but less than that which would cause an unacceptable, life threatening rise in the heart rate of said subject; and a physiologically acceptable diluent as a solvent for said peptide; said diluent also being compatible with said vasoactive amine; said composition administered for a sufficient time to increase the blood pressure of the subject to a predetermined satisfactory level, without causing an unacceptable, life threatening rise in the heart rate of the subject.

10. A method for increasing the blood pressure of a subject experiencing hypotension which comprises administering parenterally to said subject a pharmaceutical composition in the form of a solution which comprises:

a peptide of human neuropeptide Y (h-NPY) Porcine neuropeptide Y, or peptide YY (PYY); said peptide present in a therapeutically effective amount of between about 0.01 and 1 weight percent for treatment of hypotension but below that which would induce undesirable vasoconstrictor effects in said subject; and a physiologically acceptable diluent as a solvent for said peptide; said composition administered for a sufficient time to increase the blood pressure of the subject to a predetermined satisfactory level, without causing an unacceptable, life threatening rise in the heart rate of the subject.

11. The method of claim 8 or 9 wherein the amount of vasoactive amine to be administered to the subject is between about 0.001 and 1 mg/min.

12. The method of claim 7 or 8 wherein the composition includes an antibiotic agent of an amino glycoside, a cephalosporin or a broad spectrum penicillin.

13. The method of any one of claims 7 through 10 wherein the amount of peptide to be administered to the subject is between about 0.01 and 50 pmol/kg/min.

14. A method accordint to any one of claims 2 and 7–10 wherein the pharmaceutical composition is administered intravenously.

* * * * *